United States Patent
Haber et al.

[11] Patent Number: 6,066,766
[45] Date of Patent: May 23, 2000

[54] PROCESS FOR THE PREPARATION OF 4-CHLOROBIPHENYLS

[75] Inventors: Steffen Haber, Koenigstein; Stefan Scherer, Buettelborn; Andreas Meudt, Floersheim-Weilbach; Antje Noerenberg, Buettelborn, all of Germany

[73] Assignee: Clariant GmbH, Frankfurt, Germany

[21] Appl. No.: 09/366,470

[22] Filed: Aug. 3, 1999

[30] Foreign Application Priority Data

Aug. 12, 1998 [DE] Germany .................. 198 36 470

[51] Int. Cl.[7] .................... C07C 43/02; C07C 22/00; C07F 7/04

[52] U.S. Cl. .................... 568/642; 570/143; 570/190; 556/413; 548/343.5; 548/143; 548/136; 548/215; 549/29; 549/504; 558/359; 558/357; 564/183; 564/307; 546/346

[58] Field of Search .................... 570/143, 190; 568/642; 556/413; 548/343.5, 143, 136, 215; 558/359, 357; 564/307, 183; 546/346; 549/29, 504

[56] References Cited

PUBLICATIONS

Y. Ikoma et al, Synthetic Communications 21(1991),3,481–487.

*Primary Examiner*—Alan Siegel
*Attorney, Agent, or Firm*—Scott E. Hanf

[57] ABSTRACT

4-Chlorobiphenyls are prepared by reacting a haloaromatic with an aryl Grignard compound, where halogen is chlorine, bromine or iodine, in the presence of a palladium catalyst of the formula (IV)

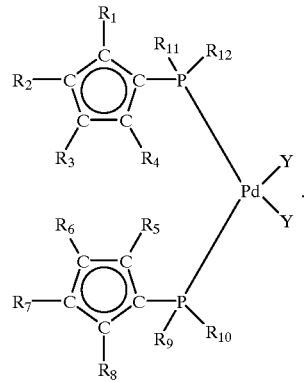

(IV)

11 Claims, No Drawings

PROCESS FOR THE PREPARATION OF 4-CHLOROBIPHENYLS

CROSS-REFERENCE TO RELATED APPLICATION

The present invention is described in the German priority application No. 198 36 470.9, filed Aug. 12, 1998, which is hereby incorporated by reference as is fully disclosed herein.

BACKGROUND OF THE INVENTION

The present invention relates to a novel process for the preparation of 4-chlorobiphenyls from haloaromatics and aryl Grignard reagents using a phosphinopalladium ferrocene catalyst. 4-Chlorobiphenyls are of industrial importance as active compound precursors for matrix metalloprotease inhibitors.

A frequently used method for the synthesis of 4-chlorobiphenyls on the laboratory scale is palladium-catalyzed cross-coupling, in which iodine and bromoaromatics are reacted with organometallic aryl derivatives, in particular arylboronic acids or aryl Grignard reagents, in the presence of palladium or nickel catalysts. Examples which describe this methodology are found, for example, in Y. Ikoma et al., Synthetic Commun. 21 (1991), 3,481–487.

Despite the large number of publications in the field of the synthesis of 4-chlorobiphenyls in the presence of nickel or palladium catalysts, to date no 25 examples of a relatively large industrial transposition of the methods are known. This is to be attributed to the fact that the catalyst systems described can frequently only be employed with uneconomical amounts of catalysts or low selectivities, i.e. high rates of dimerization products and dechlorinated products (A. Hutz et al., Tetrahedron, 45, 21, 1989, 6679–6682). Otherwise, large amounts of catalyst—generally >1 mol %—must be added in order to achieve industrially utilizable conversions. On account of the complexity of the reaction mixtures, simple recycling of catalyst is moreover not possible, so that catalyst costs as a rule prevent industrial realization.

Moreover, aryl transfers are observed as a side reaction in the Suzuki coupling of substituted biphenyls using customary catalyst systems, such as Pd(OAc)$_2$/triphenylphosphane mixtures (O'Keefe et al., Tetrahedron Letters 1992, 6679).

SUMMARY OF THE INVENTION

For the reasons mentioned, it is of great industrial interest to find better, industrially utilizable catalyst systems for the synthesis of 4-chlorobiphenyls, in particular for the arylation of economically favorable bromo- and chloroaromatics. There is thus a great need for a process which avoids the disadvantages described and makes 4-chlorbiphenyls accessible in high purity in an industrially simple manner.

DESCRIPTION OF THE PREFERRED EMBODIMENTS

This object is achieved by a process for the preparation of 4-chlorobiphenyls of the formula (I)

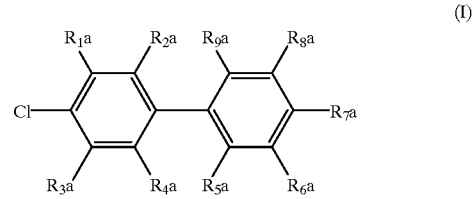

(I)

in which $R_1a$ to $R_4a$ are identical or different and have the meaning hydrogen, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-acyloxy, O-phenyl, O-benzyl, aryl, heteroaryl, F, Cl, NO$_2$, CN, SO$_2$R, SOR, NH($C_1$–$C_6$-alkyl), N($C_1$–$C_6$-alkyl)$_2$, C=N($C_1$–$C_6$-alkyl), CX$_3$, COO—($C_1$–$C_{12}$-alkyl), CO—($C_1$–$C_{12}$-alkyl), CO-phenyl, COO-phenyl, CON($C_1$–$C_8$-alkyl)$_2$, CONH ($C_1$–$C_8$-alkyl), CHCHCOO—($C_1$–$C_{12}$-alkyl), N(Si($C_1$–$C_4$-alkyl)$_3$), PO(phenyl)$_2$, PO—($C_1$–$C_8$-alkyl)$_2$ or PO$_3$—($C_1$–$C_8$-alkyl)$_2$, where R is aryl, preferably phenyl or naphthyl, F or C$_n$F$_{2n+1}$ where n=1 to 12, and where X is F, Cl or Br; $R_5a$ to $R_9a$ are identical or different and have the meaning hydrogen, $C_1$–$C_{12}$-alkyl, $C_2$–$C_{12}$-alkenyl, $C_2$–$C_{12}$-alkynyl, $C^1$–$C_{12}$-alkoxy, O-phenyl, O-benzyl, aryl, heteroaryl, F, Cl, NO$_2$, CN, SO$_2$R, SOR, where R is aryl, preferably phenyl or naphthyl, which comprises reacting a haloaromatic of the formula (II)

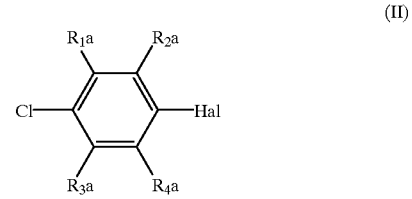

(II)

with an aryl Grignard compound of the formula (III)

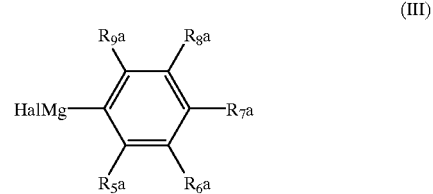

(III)

in which Hal is chlorine, bromine or iodine, in the presence of a palladium catalyst of the formula (IV)

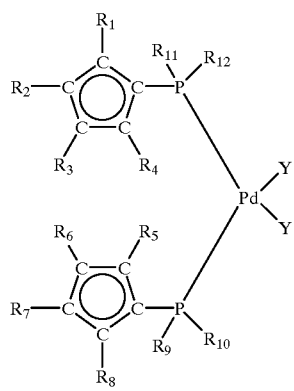

in which $R_1$ to $R_8$ are identical or different and are hydrogen, $(C_1–C_4)$-alkyl, $(C_5–C_8)$-cycloalkyl, $(C_1–C_4)$-alkoxy, fluorine, $NH_2$, $NH$-$(C_1–C_4$-alkyl), $N(C_1–C_4$-alkyl$)_2$, $CO_2$-alkyl-$(C_1–C_4)$ or phenyl, or $R_1$ and $R_2$, or $R_2$ and $R_3$, or $R_3$ and $R_4$; and/or $R_5$ and $R_6$, or $R_6$ and $R_7$, or $R_7$ and $R_8$ together form an aliphatic or aromatic ring, Rg to $R_{12}$ are identical or different and are $C_1–C_8$-alkyl, $C_3–C_{12}$-cycloalkyl or aryl which can be substituted by 1 to 3 substituents from the group consisting of $C_1–C_4$-alkyl, $C_1–C_4$-alkoxy and halogen, and Y is an anion of an organic or inorganic acid.

A preferred process for the preparation of compounds of the formula (I) is one in which $R_1a$ to $R_4a$ are hydrogen, $C_1–C_8$-alkyl, $C_1–C_8$-alkoxy, F, Cl, CN, a 5- or 6-membered heteroaryl having 1 to 3 heteroatoms from the group consisting of O, S and N, COO—$(C_1–C_8$-alkyl), CONH$(C_1–C_4$-alkyl) or CON$(C_1–C_4$-alkyl$)_2$ and in which $R_5a$ to $R_9a$ are hydrogen, $C_1–C_6$-alkyl, $C_2–C_6$-alkenyl, $C_1–C_6$-alkoxy, O-phenyl, O-benzyl, F, Cl, NH$(C_1–C_4$-alkyl) or N$(C_1–C_4$-alkyl$)_2$.

A particularly preferred process for the preparation of compounds of the formula (I) is one in which $R_1a$ to $R_4a$ are hydrogen, $C_1–C_4$-alkyl, $C_1–C_4$-alkoxy, CN, COO$(C_1–C_4$-alkyl), phenyl, thiophenyl, furanyl, imidazolyl, oxadiazolyl, thiadiazolyl, oxazolyl, 4,5-dihydrooxazolyl, pyridyl, CONH $(C_1–C_2$-alkyl), CON$(C_1–C_2$-alkyl$)_2$, F or Cl and in which $R_5a$ to $R_9a$ are hydrogen, $C_1–C_4$-alkyl, $C_1–C_6$-alkoxy, O-phenyl, O-benzyl, F, Cl, NH$(C_1–C_2$-alkyl) or N$(C_1–C_2$-alkyl$)_2$.

A process which is of very particular interest is one for the preparation of 4-chlorobiphenyl, 4-chloro-4'-methylbiphenyl or 4-chloro-4'-n-pentoxybiphenyl or 4-chloro-2-methylbiphenyl.

Preferred catalysts are those of the formula (IV) in which $R_1$ to $R_8$ are hydrogen, methyl, ethyl, $(C_5–C_6)$-cycloalkyl, methoxy, ethoxy, fluorine, NH$(C_1–C_2$-alkyl), N$(C_1–C_2$-alkyl$)_2$, phenyl, and $R_9$, $R_{10}$, $R_{11}$, $R_{12}$ are phenyl, tolyl, xylyl, mesityl, fluorophenyl or $(C_1–C_4)$-alkoxyphenyl, and Y is chloride, bromide, iodide, fluoride, acetate, propionate, benzoate, sulfate, hydrogensulfate, nitrate, phosphate, tetrafluoroborate, tosylate, mesylate, acetylacetonate, hexafluoroacetylacetonate, trifluoracetate or pyrazolyl.

Particularly preferred compounds are those of the formula (IV) in which $R_1$ to $R_8$ are H, methyl or phenyl, and $R_9$ to $R_{12}$ are phenyl, tolyl, xylyl, fluorophenyl or methoxyphenyl.

The following are very particularly preferred:
1,1'-bis(diphenylphosphino)ferrocenepalladium(II) chloride (=Pd (dppf)Cl$_2$),
1,1'-bis(diphenylphosphino)ferrocenepalladium(II) chlorideedichloro-methane and
1,1'-bis(diphenylphosphino)ferrocenepalladium(II) bromide.

Relative to the haloaromatics of the formula (II), the catalyst is expediently employed in a $10^{-6}$ to 1-fold, preferably in a $10^{-5}$ to 0.1-fold, in particular in a 0.0001 to 0.01-fold, molar amount. The catalyst is preferably employed in the homogeneous phase. Solvents which are used are generally inert organic solvents. Aromatic solvents are preferably employed, such as alkyl-, dialkyl- or trialkylbenzenes, or polar aprotic solvents, e.g. ethers, such as tetrahydrofuran, tert-butyl methyl ether, diethyl ether, diethylene glycol dimethyl ether or dimethoxyethane.

The palladium catalysts employed can be synthesized before the reaction according to the invention; however, they can also be produced in situ without loss of catalytic activity. The synthesis of the catalyst is carried out, for example, analogously to A. W. Rudie, D. W. Lichtenberg, M. L. Katcher, A. Davison, Inorg. Chem. 17, 1978, 2859. Mixtures of these catalysts can also be employed.

The process according to the invention is in general carried out at temperatures from 20 to 200° C. Temperatures from 60 to 180° C., in particular 60 to 100° C., are preferred.

The metered addition of the Grignard components, dissolved in an inert solvent, to the haloaromatic and the catalyst in a solvent which is inert to all reactants is of particular advantage. Suitable inert solvents are preferably those mentioned above for the catalyst.

The Grignard compounds employed are advantageously employed as 15 to 40% strength by weight solutions, e.g. in tetrahydrofuran. 20 to 35% strength by weight solutions in tetrahydrofuran are of particular advantage.

The molar quantitative ratios between the haloaromatics of the formula (II) and the Grignard compounds of the formula (III) are expediently 1:1 to 1:1.3, preferably 1:1.001 to 1:1.01.

The process according to the invention affords the desired products in very good yields with very good conversions and selectivitives. By-products during the reaction, formed by dimerization of the Grignard components or dimerization of the haloaromatics or by secondary reactions of the 4-chlorobiphenyls with excess Grignard reagent, are only observed on a minor scale (<1%).

The compounds needed as starting substances are known and can be prepared by methods known per se.

EXAMPLES

Example 1

(4-Chlorobiphenyl)

6 mol of a 26% strength by weight phenylmagnesium chloride/THF solution are added dropwise in the course of 4 hours to a boiling solution of 6 mol of 1,4-bromochlorobenzene and 100 mg of Pd(dppf)Cl$_2$*CH$_2$Cl$_2$ in 600 g of tetrahydrofuran (THF). After completion of the addition, the reaction mixture is refluxed for a further 5 hours. After hydrolysis with 3600 g of 8% strength by weight sulfuric acid, phase separation and subsequent removal of the solvent by distillation, crude 4-chlorobiphenyl is obtained, which is purified by fractional distillation in vacuo. Yield 1080 g (96%), purity of the product □ 99.7% (a/a GC).

Example 2

(4,4'-Dichlorobiphenyl)

0.5 mol of a 25% strength by weight 4-chlorophenylmagnesium chloride/THF solution is added dropwise in the course of 30 minutes to a boiling solution of 0.5 mol of 1,4-bromochlorobenzene and 0.25 g of Pd(dppf)Cl$_2$*CH$_2$Cl$_2$ in 100 ml of THF. After stirring under reflux for four hours, the mixture is hydrolyzed with dilute sulfuric acid (conversion 99%, selectivity 98%). The organic phase is freed from the solvent by distillation. The crude 4,4'-dichlorobiphenyl thus obtained is recrystallized from ethanol.

Example 3

(4-Chloro-4'-methylbiphenyl)

0.5 mol of a 25% strength by weight 4-methylphenylmagnesium chloride/THF solution is added dropwise in the course of 30 minutes to a boiling solution of 0.5 mol of 1,4-bromochlorobenzene and 0.0025 g of Pd(dppf)Cl$_2$*CH$_2$Cl$_2$ in 100 ml of THF. After stirring under reflux for four hours, the mixture is hydrolyzed with dilute sulfuric acid (conversion 99%, selectivitity 97%). The organic phase is freed from the solvent by distillation. The crude 4-chloro-4'-methylbiphenyl thus obtained is recrystallized from ethanol.

Example 4

(4-Chloro-4'-n-pentoxybiphenyl)

0.5 mol of a 25% strength by weight 4-n-pentoxyphenylmagnesium chloride/THF solution is added dropwise in the course of 30 minutes to a boiling solution of 0.5 mol of 1,4-bromochlorobenzene and 0.0025 g of Pd(dppf)Cl$_2$*CH$_2$Cl$_2$ in 100 ml of THF. After stirring under reflux for four hours, the mixture is hydrolyzed with dilute sulfuric acid (conversion 99%, selectivitity 97%). The organic phase is freed from the solvent by distillation. The 4-chloro-4'-pentoxybiphenyl thus obtained is recrystallized from ethanol.

Example 5

(4-Chloro-3'-bis(trimethylsilyl)aminobiphenyl)

0.5 mol of a 25% strength by weight 3-bis(trimethylsilyl)aminophenyl-magnesium chloride/THF solution is added dropwise in the course of 30 minutes to a boiling solution of 0.5 mol of 1,4-bromochlorobenzene and 0.0025 g of Pd(dppf)Cl$_2$*CH$_2$Cl$_2$ in 100 ml THF. After stirring under reflux for four hours, the mixture is hydrolyzed with dilute sulfuric acid (conversion 99%, selectivity 97%). The organic phase is freed from the solvent by distillation. The crude 4-chloro-3'-bis(trimethylsilyl)aminobiphenyl thus obtained is recrystallized from isopropanol.

Example 6

Preparation of 4-chloro-2-methylbiphenyl 1.03 mol of a phenylmagnesium chloride solution (26% by weight in THF) are added dropwise in the course of 60 minutes to a boiling solution of 1.0 mol of 2-bromo-5-chlorotoluene and 0.2 g of Pd(dppf) Cl$_2$*CH$_2$Cl$_2$ in 200 ml of THF. After stirring under reflux for eight hours (conversion >97%), the mixture is hydrolyzed with water. After purification by distillation, 4-chloro-2-methylbiphenyl is obtained as a colorless liquid in a yield of 89%.

What is claimed is:

1. A process for the preparation of 4-chlorobiphenyls of the formula (I)

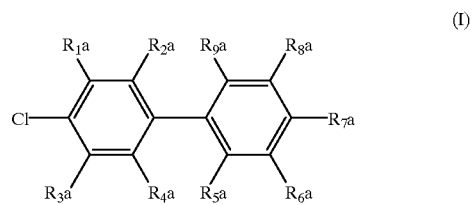

in which R$_1$a to R$_4$a are identical or different and have the meaning hydrogen, C$_1$–C$_{12}$-alkyl, C$_2$–C$_{12}$-alkenyl, C$_2$–C$_{12}$-alkynyl, C$_1$–C$_{12}$-alkoxy, C$_1$–C$_{12}$-acyloxy, O-phenyl, O-benzyl, aryl, heteroaryl, F, Cl, NO$_2$, CN, SO$_2$R, SOR, NH(C$_1$–C$_6$-alkyl), N(C$_1$–C$_6$-alkyl)$_2$, C=N(C$_1$–C$_6$-alkyl), CX$_3$, COO—(C$_1$–C$_{12}$-alkyl), CO—(C$_1$–C$_{12}$-alkyl), CO-phenyl, COO-phenyl, CON(C$_1$–C$_8$-alkyl)$_2$, CONH(C$_1$–C$_8$-alkyl), CHCHCOO—(C$_1$–C$_{12}$-alkyl), N(Si(C$_1$–C$_4$-alkyl)$_3$), PO(phenyl)$_2$, PO—(C$_1$–C$_8$-alkyl)$_2$ or PO$_3$—(C$_1$–C$_8$-alkyl)$_2$, where R is aryl, F or C$_n$F$_{2n+1}$ where n=1 to 12, and where X is F, Cl or Br; and R$_5$a to R$_9$a are identical or different and have the meaning hydrogen, C$_1$–C$_{12}$-alkyl, C$_2$–C$_{12}$-alkenyl, C$_2$–C$_{12}$-alkynyl, C$_1$–C$_{12}$-alkoxy, O-phenyl, O-benzyl, aryl, heteroaryl, F, Cl, NO$_2$, CN, SO$_2$R, SOR, where R is aryl, which comprises reacting a haloaromatic of the formula (II)

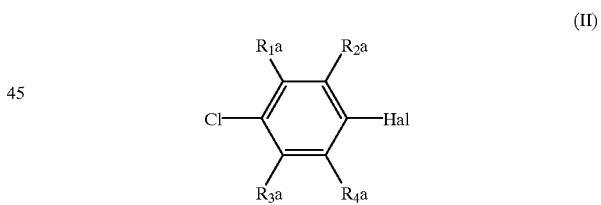

with an aryl Grignard compound of the formula (III)

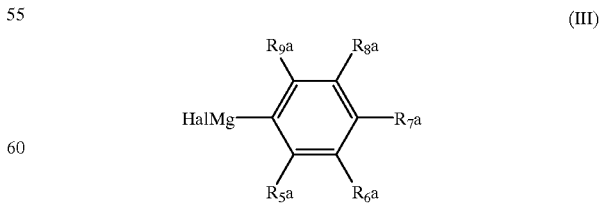

in which Hal is chlorine, bromine or iodine, in the presence of a palladium catalyst of the formula (IV)

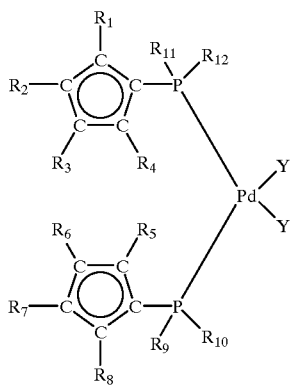

(IV)

in which $R_1$ to $R_8$ are identical or different and are hydrogen, $(C_1-C_4)$-alkyl, $(C_5-C_8)$-cycloalkyl, $(C_1-C_4)$-alkoxy, fluorine, $NH_2$, $NH-(C_1-C_4$-alkyl), $N(C_1-C_4$-alkyl)$_2$, $CO_2$-alkyl-$(C_1-C_4)$ or phenyl, or $R_1$ and $R_2$, or $R_2$ and $R_3$, or $R_3$ and $R_4$; and optionally $R_5$ and $R_6$, or $R_6$ and $R_7$, or $R_7$ and $R_8$ together form an aliphatic or aromatic ring, $R_9$ to $R_{12}$ are identical or different and are $C_1-C_8$-alkyl, $C_3-C_{12}$-cycloalkyl or aryl which is optionally substituted by 1 to 3 substituents selected from the group consisting of $C_1-C_4$-alkyl, $C_1-C_4$-alkoxy and halogen, and Y is an anion of an organic or inorganic acid.

2. The process as claimed in claim 1, wherein $R_1a$ to $R_4a$ are hydrogen, $C_1-C_8$-alkyl, $C_1-C_8$-alkoxy, F, Cl, CN, a 5- or 6-membered heteroaryl having 1 to 3 heteroatoms from the group consisting of O, S and N, COO—$(C_1-C_8$-alkyl), CONH$(C_1-C_4$-alkyl) or CON$(C_1-C_4$-alkyl)$_2$ and in which $R_5a$ to $R_9a$ are hydrogen, $C_1-C_6$-alkyl, $C_2-C_6$-alkenyl, $C_1-C_6$-alkoxy, O-phenyl, O-benzyl, F, Cl, NH$(C_1-C_4$-alkyl) or N$(C_1-C_4$-alkyl)$_2$.

3. The process as claimed in claim 1, wherein $R_1a$ to $R_4a$ are hydrogen, $C_1-C_4$-alkyl, $C_1-C_4$-alkoxy, CN, COO $(C_1-C_4$-alkyl), phenyl, thiophenyl, furanyl, imidazolyl, oxadiazolyl, thiadiazolyl, oxazolyl, 4,5-dihydrooxazolyl, pyridyl, CONH$(C_1-C_2$-alkyl), CON$(C_1-C_2$-alkyl)$_2$, F or Cl and in which $R_5a$ to $R_9a$ are hydrogen, $C_1-C_4$-alkyl, $C_1-C_6$-alkoxy, O-phenyl, O-benzyl, F, Cl, NH$(C_1-C_2$-alkyl) or N$(C_1-C_2$-alkyl)$_2$.

4. The process as claimed in claim 1, wherein the compound of the formula (I) is 4-chlorobiphenyl, 4-chloro-4'-methylbiphenyl, 4-chloro-2-methylbiphenyl or 4-chloro-4'-n-pentoxybiphenyl.

5. The process as claimed in claim 1, wherein, in the compound of the formula (IV), $R_1$ to $R_8$ are hydrogen, methyl, ethyl, $(C_5-C_6)$-cycloalkyl, methoxy, ethoxy, fluorine, NH$(C_1-C_2$-alkyl), N$(C_1-C_2$-alkyl)$_2$, phenyl, and $R_9$, $R_{10}$, $R_{11}$, $R_{12}$ are phenyl, tolyl, xylyl, mesityl, fluorophenyl or $(C_1-C_4)$-alkoxyphenyl, and Y is chloride, bromide, iodide, fluoride, acetate, propionate, benzoate, sulfate, hydrogensulfate, nitrate, phosphate, tetrafluoroborate, tosylate, mesylate, acetylacetonate, hexafluoroacetylacetonate, trifluoracetate or pyrazolyl.

6. The process as claimed in claim 1, wherein, in the compound of the formula (IV), $R_1$ to $R_8$ are H, $CH_3$ or phenyl, and $R_9$ to $R_{12}$ are phenyl, tolyl, xylyl, fluorophenyl or methoxyphenyl.

7. The process as claimed in claim 1, wherein the catalyst of the formula (IV) is 1,1'-bis(diphenylphosphino)ferrocene,palladium(II) chloride, 1,1'-bis(diphenylphosphino)ferrocenepalladium(II) chlorideΩdichloro-methane or 1,1'-bis(diphenylphosphino)ferrocenepalladium(II) bromide.

8. The process as claimed in claim 1, wherein the catalyst of the formula (IV) is employed in a $10^{-6}$ to 1-fold, molar amount, relative to the haloaromatics of the formula (II).

9. The process as claimed in claim 1, wherein the catalyst of the formula (IV) is employed in a $10^{-5}$ to 0.1-fold, molar amount, relative to the haloaromatics of the formula (II).

10. The process as claimed in claim 1, wherein the reaction is carried out in an aromatic solvent or an ether.

11. The process as claimed in claim 1, wherein the aryl Grignard compound of the formula (III) is dissolved in an inert solvent and is added to the haloaromatic of the formula (II) and the catalyst of the formula (IV).

* * * * *